(12) United States Patent
Bint

(10) Patent No.: US 6,626,869 B1
(45) Date of Patent: Sep. 30, 2003

(54) GUIDE WIRE INTRODUCER

(75) Inventor: Stephen Bint, Chippenham (GB)

(73) Assignee: Becton Dickinson Critical Care System PTE Ltd. (SG)

( * ) Notice: Subject to any disclaimer, the term of this patent is extended or adjusted under 35 U.S.C. 154(b) by 0 days.

(21) Appl. No.: 09/508,276

(22) PCT Filed: Sep. 9, 1998

(86) PCT No.: PCT/GB98/02723

§ 371 (c)(1),
(2), (4) Date: May 19, 2000

(87) PCT Pub. No.: WO99/12600

PCT Pub. Date: Mar. 18, 1999

(30) Foreign Application Priority Data

Sep. 9, 1997 (GB) .............................................. 9719182

(51) Int. Cl.$^7$ ........................ A61M 5/178; A61M 25/00; A61M 5/00; A61B 17/50
(52) U.S. Cl. .................. 604/164.01; 604/213; 604/264; 604/158; 604/160; 606/213
(58) Field of Search ................................ 604/160, 161, 604/158, 509, 101.04, 28, 212, 167.01, 167.03, 187, 207, 164.13, 164.01, 264, 506, 170.03, 165.02, 164.14, 198, 213; 606/213; 600/585, 481, 575

(56) References Cited

U.S. PATENT DOCUMENTS

| 5,221,269 A | * | 6/1993 | Miller et al. ........... 604/170.03 |
| 5,527,291 A | * | 6/1996 | Zadini et al. ................ 604/158 |
| 5,579,780 A | * | 12/1996 | Zadini et al. ................ 600/585 |
| 5,749,371 A | * | 5/1998 | Zadini et al. ................ 600/481 |
| 6,056,769 A | * | 5/2000 | Epstein et al. ............... 606/213 |

* cited by examiner

Primary Examiner—Michael J. Hayes
Assistant Examiner—Roz Ghafoorian
(74) Attorney, Agent, or Firm—James J. Murtha

(57) ABSTRACT

The present invention comprises a device for advancing a guide wire into a blood vessel of a patient, which comprises a housing from a distal end of which extends a needle hub support having a blood aspiration canal extending along its length; a syringe chamber located in the housing; a passageway extending between the blood aspiration canal and the syringe chamber for the passage therethrough of aspirated blood; a switch mounted for sliding movement along a surface of the housing and having attached thereto a cannula for movement therewith; the switch being formed with a through hole aligned with the cannula and the blood aspiration canal for the passage therethrough of a guide wire; the arrangement being such that movement of the switch towards the distal end of the housing will cause the cannula to block the passage of blood along the passageway between the blood aspiration canal and the syringe chamber.

16 Claims, 20 Drawing Sheets

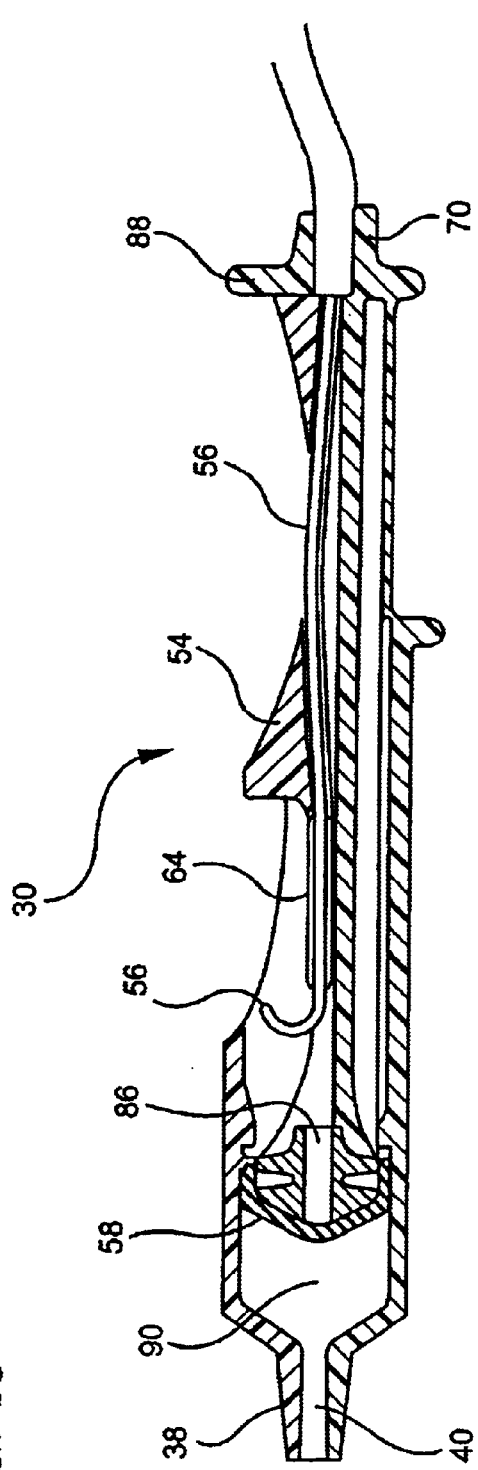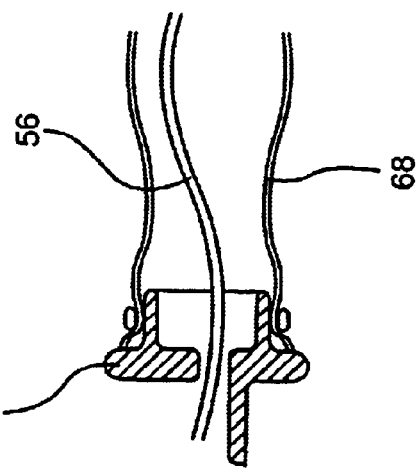
FIG. 19
FIG. 20

GUIDE WIRE INTRODUCER

BACKGROUND OF THE INVENTION

The present invention relates to guide wire introducers which are medical devices for the insertion of a guide wire into the blood vessel of a patient.

Guide wires are used so that a cannula which is mounted over the guide wire can be slidably moved along the guide wire for insertion into the blood vessel of a patient. The guide wire is subsequently withdrawn from the blood vessel through the cannula leaving the cannula within the blood vessel.

Known guide wire insertion devices or introducers suffer from problems arising from the difficulties of manipulation and the exposure of the guide wire to possible contamination prior to insertion into the blood vessel. Obviously, it is important to be able to manipulate the guide wire into the patient's blood vessel with a minimum of tedious manoeuvres while, at the same time, it is important to isolate the guide wire from any contamination during the process to prevent that contamination from entering the blood vessel of the patient and do harm to the patient.

In a currently available guide wire introducer, access to the blood vessel of the patient is first established using a percutaneous needle introducer with an attached syringe. Confirmation that the needle has pierced the blood vessel is established when blood can be seen freely aspirating into the syringe. The syringe is then removed which requires a change of grip on the introducer and increases the chances for misplacement of the needle tip which might cause damage to the blood vessel wall, blood loss, air embolism and increased procedure time. Subsequently the syringe is discarded. However it may contain aspirated blood which poses the potential risk of contamination or harm to the attending personnel especially if the syringe plunger is depressed accidentally. In such case, the patient's blood can contact the personnel and pose a health risk to those persons.

The guide wire itself is normally provided in a coiled, protective tube. The diameter of the coil assembly is bulky and can hinder access to the introducer. This known guide wire introducer uses a J tip Seldinger guide wire which has its end formed into the shape of a J. That configuration has to be straightened before introduction into the needle. This is normally achieved by pulling the wire backwards into a straightener and then moving the wire forwardly into the desired location within the patient. Manipulation of the guide wire through the straightener and needle introducer involves a high degree of care and experience.

The whole introduction procedure may require assistance by nursing staff as additional hands are often required to hold the introducer needle in the blood vessel whilst straightening and advancing the guide wire.

BRIEF SUMMARY OF THE INVENTION

It is an aim of the present invention to provide a device for advancing a guide wire into a blood vessel of a patient which removes or mitigates against the disadvantages mentioned above in connection with the currently available guide wire introducer.

According to the present invention, a device for advancing a guide wire into a blood vessel of a patient comprises a housing from a distal end of which extends a needle hub support having a blood aspiration canal extending along its length; a syringe chamber located in the housing; a passageway extending between the blood aspiration canal and the syringe chamber for the passage therethrough of aspirated blood; a switch mounted for sliding movement along a surface of the housing and having attached thereto a cannula for movement therewith; the switch being formed with a through hole aligned with the cannula and the blood aspiration canal for the passage therethrough of a guide wire; the arrangement being such that movement of the switch towards the distal end of the housing will cause the cannula to block the passage of blood along the passageway between the blood aspiration canal and the syringe chamber.

In a preferred embodiment a seal is provided preventing the flow of aspirated blood along the blood aspiration canal and over the housing, movement of the switch towards the distal end of the using causing the cannula to pierce the seal to allow the passage of the guide wire through the canal.

In a preferred embodiment, lugs are provided on the surface of the housing one at the distal end and the remaining lug at the proximal end of the housing, each lug being formed with a through hole in alignment with the through hole in the switch for guiding the guide wire.

Preferably, the switch is slidably mounted on rails formed on the housing between the lugs and over said surface which is substantially flat.

In a preferred embodiment a flexible envelope is attached to the proximal end of the housing and surrounds that portion of the guide wire extending outwardly from the proximal end of the housing. Thus, the guide wire is protected from contamination by the flexible envelope.

BRIEF DESCRIPTION OF THE DRAWINGS

An embodiment of the invention will now be described by way of example, reference being made to the Figures of the accompanying diagrammatic drawings in which:

FIG. 19 is a side cross sectional view of the embodiment of FIG. 18;

FIG. 20 is an enlarged side cross sectional view of a portion of the embodiment of FIGS. 18 and 19.

DETAILED DESCRIPTION OF THE INVENTION

Figure 1:
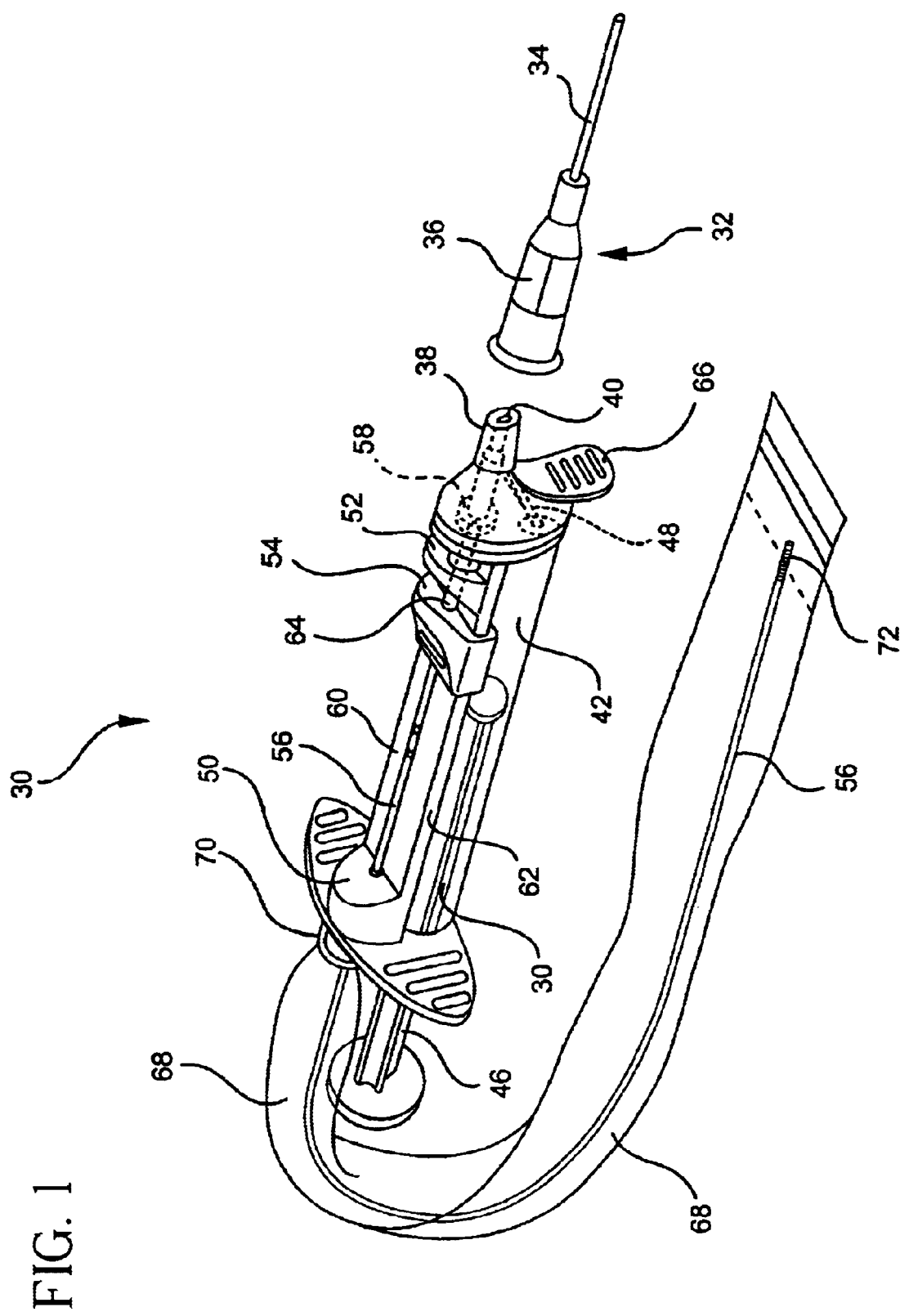
FIG. 1 is a perspective sketch of a guide wire guide introducer according to the present invention.
Figure 2:
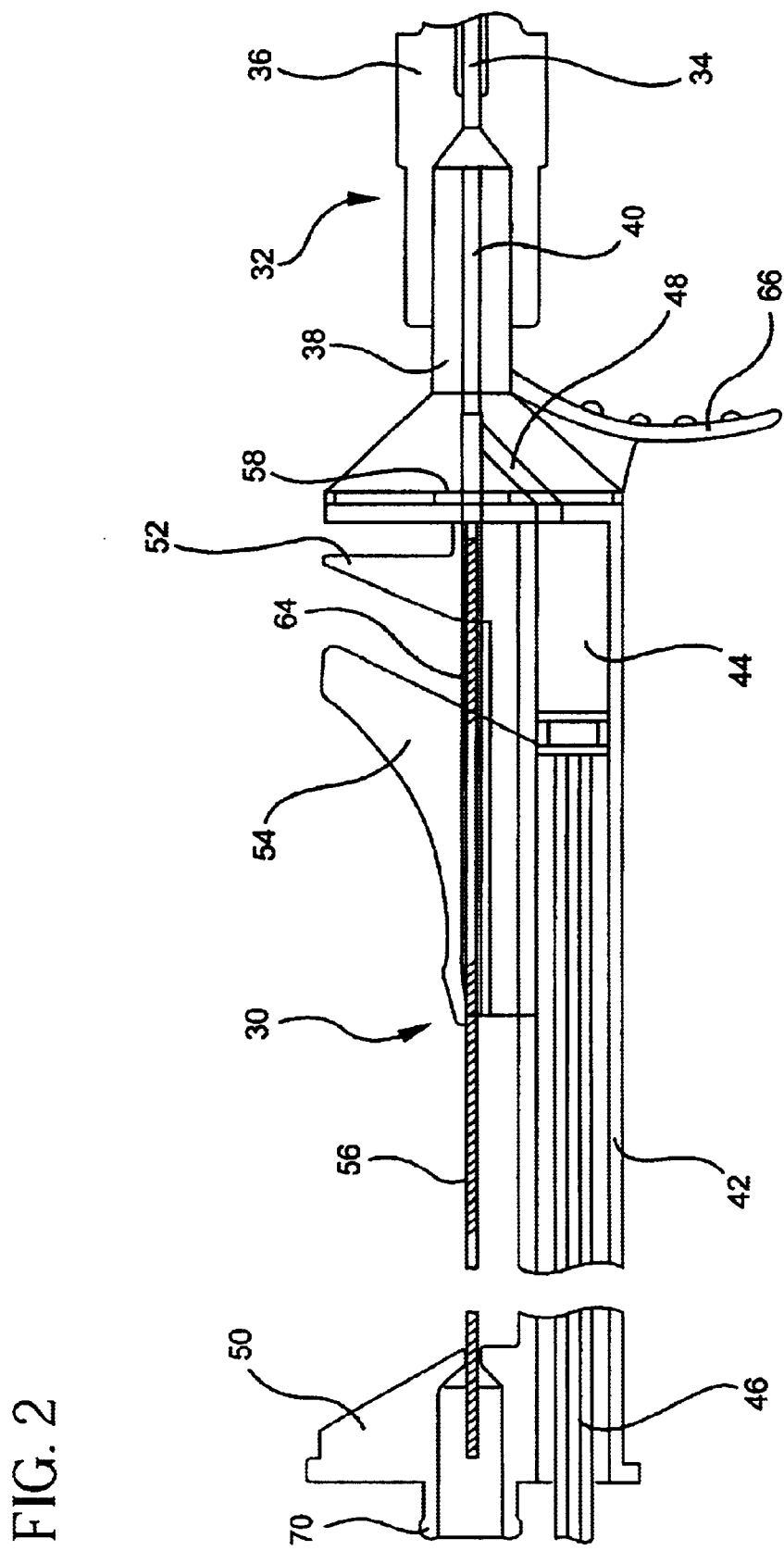
FIG. 2 is a longitudinal cross-section through the guide wire guide introducer of FIG. 1.
Figure 3:
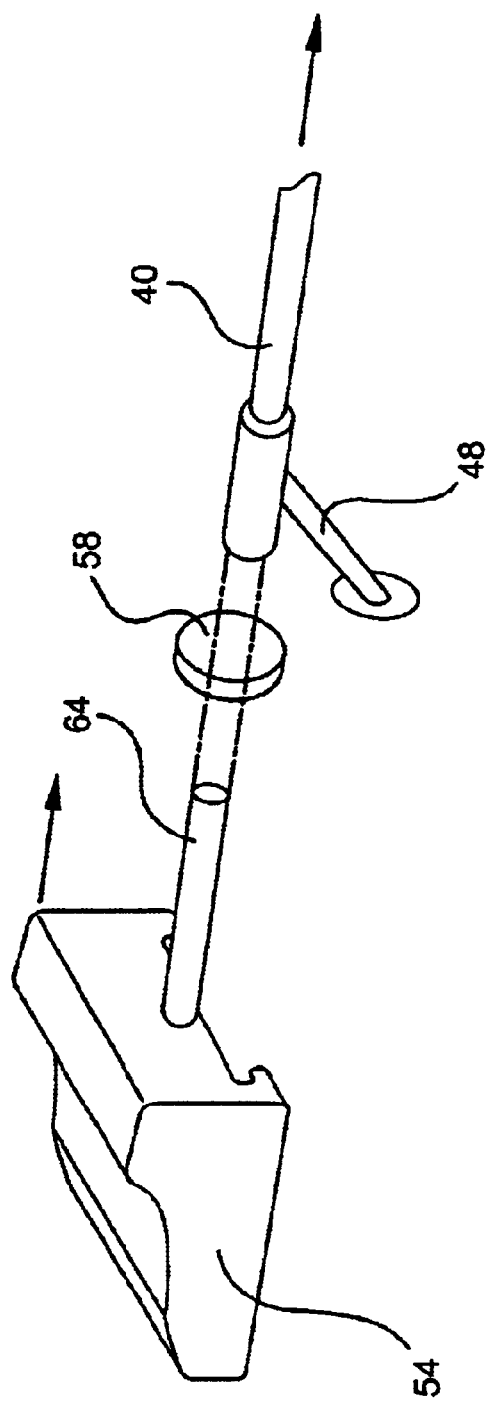
FIG. 3 is an enlarged, perspective detail of a thumb switch forming part of the guide wire introducer of FIGS. 1 & 2.

Turning first to FIGS. 1–3, there is shown a guide wire introducer 30 adapted to receive, at its distal end, a needle assembly 32. The needle assembly 32 comprises a hollow needle 34 attached to a needle hub 36. As shown, the needle hub 36 fits over a needle hub support 38 and is supported thereon at the distal end of the guide wire introducer 30. As used throughout the present specification, the distal end of a guide wire introducer 30 will refer to the end of the device that is directed toward the patient during use and the proximal end will refer to the opposite end that extends away from the patient. A blood aspiration canal 40 extends through the needle hub support 38 and, when the needle hub 36 is affixed to the distal end of the guide wire introducer 30, the blood aspiration canal 40 also communicates with the hollow needle 34 so as to withdraw blood from the patient as will be explained. The needle hub support 38, as shown, extends forwardly from the distal end of guide wire introducer housing 42. The guide wire introducer housing 42 is formed with an internal syringe chamber 44 along which a syringe plunger 46 can be slidably moved in a longitudinal sense. A passageway 48 extends between the internal syringe chamber 44 and the blood aspiration canal 40.

Mounted on the guide wire introducer housing 42 at its proximal and distal ends are lugs 50,52 and between the lugs 50,52 there is mounted a thumb switch 54 The lugs 50, 52 and the thumb switch 54 are all formed with aligned holes through which can pass a guide wire 56. The holes as shown are in turn aligned with the blood aspiration canal 40 but are initially separated therefrom by the means of a seal 58. The thumb switch 54 is movable longitudinally of the guide wire introducer housing 42 over a flat surface 60 on guide rails 62 (only one of which is shown in FIG. 1) extending between the lugs 50,52. The thumb switch 54 carries with it a piercing cannula 64 that extends distally from the thumb switch 54.

A finger support 66 is provided at the distal end of the guide wire introducer housing 42. A foil or flexible envelope 68 surrounds the guide wire 56 extending from the proximal end of the guide wire introducer housing 42 and is attached to the proximal end of the guide wire introducer 30 by a securing ring 70.

In use, the forward tip of the guide wire 56 is threaded through the aligned holes in the lug 50, thumb switch 54 and lug 52 so that it is located in the piercing cannula 64. The guide wire introducer 30 can be held in either hand with a fore-finger engaging the finger support 66 and a thumb over the flat surface 60 of the guide wire introducer housing 42 between the lugs 50,52.

The distal tip of the hollow needle 34 is caused to pierce the skin of a patient and enter a blood vessel. At the same time, the syringe plunger 46 is withdrawn from the internal syringe chamber 44 until blood can be seen aspirating into the internal syringe chamber 44 via the blood aspiration canal 40 and the passageway 48. When entry of the hollow needle 34 into the blood vessel has been confirmed by the user noting the presence of blood in the internal syringe chamber 44, the thumb of the user is slid over the flat surface 60 of the guide wire introducer housing 42 and the thumb switch 54 is pushed forwardly such that the piercing cannula 64 pierces the seal 58 and extends beyond the junction of the blood aspiration canal 40 and the passageway 48. The outer diameter of the piercing cannula 64 matches the inner diameter of the blood aspiration canal 40 and thus isolates the internal syringe chamber 44 so that the syringe cannot be accidentally discharged and the aspirated blood blown out of the internal syringe chamber 44. In other words the aspirated blood is trapped within the internal syringe chamber 44 and is blocked with respect to the blood aspiration canal 40.

The guide wire 56 is thus advanced into the blood vessel through the seal 58 and blood aspiration canal 40 and the hollow needle 34. This can be achieved without any change of grip by the user on the guide wire introducer 30. As is normal, the guide wire can thus be advanced into the patient by a simple manipulation by the user's thumb frictionally engaging the wire and manipulating it forward toward the distal end of the guide wire introducer 30.

Preferably the guide wire introducer 30 is molded from a transparent or translucent material so that the length of the guide wire 56 can be seen at various points through the guide wire introducer 30. That distance is readily apparent by means of standard markings on guide wires to inform the user as to the length of guide wire that is being extended from the introducer.

It will be apparent that that portion of the guide wire 56 which extends from the proximal end of the guide wire introducer housing 42 is protected from contamination by the clear flexible envelope 68.

In the event that it is desired to use the straight end 72 of the guide wire 56, the distal end of the sheath flexible envelope 68 can be torn off so that the guide wire 56 and the flexible envelope 68 can be removed from the guide wire introducer 30. The flexible envelope 68 can be readily uncoupled from the proximal end of the guide wire introducer housing 42 by pulling off the securing ring 70. The guide wire 56 and the flexible envelope 68 can be turned around and the straight end 72 of the guide wire 56 re-inserted into the guide wire introducer 30. Thus, the guide wire 56 can be used having a J end and a straight end 72 and either end may be introduced into the patient by means of the present invention easily and without undue manipulation by the user.

Alternatively the guide wire 56 be removed totally from the guide wire introducer 30 and used separately.

The guide wire introducer 30 as described in this embodiment is user-friendly in that it requires only a single step operation. There is no guide wire coil assembly to interfere with the insertion procedure. In addition, the flexible envelope 68 prevents contamination of the guide wire 56 prior to entry into the blood vessel of the patient and any aspirated blood is contained safely within the internal syringe chamber 44 to alleviate the potential problem of contamination of areas of the insertion site and to protect the users of the guide wire introducer 30 from inadvertent contact with the blood of the patient.

Figure 4:
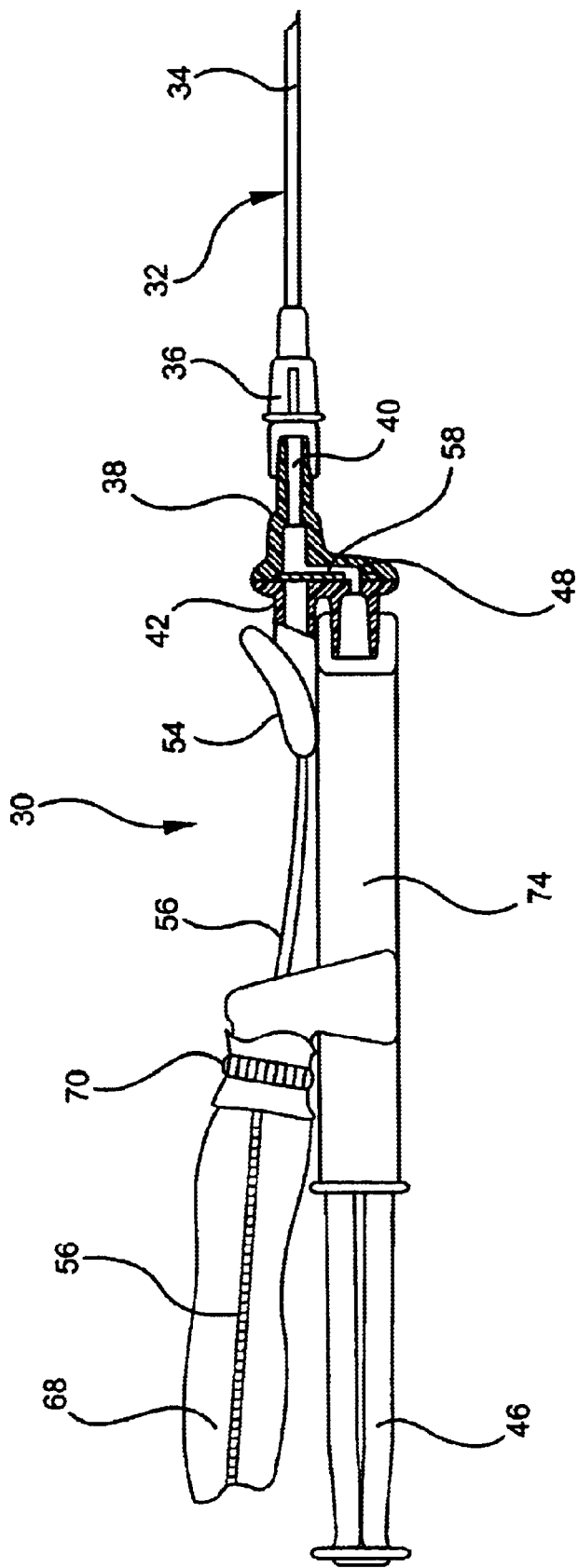
FIG. 4 is a side view of a further embodiment of the subject invention.
Figure 5:
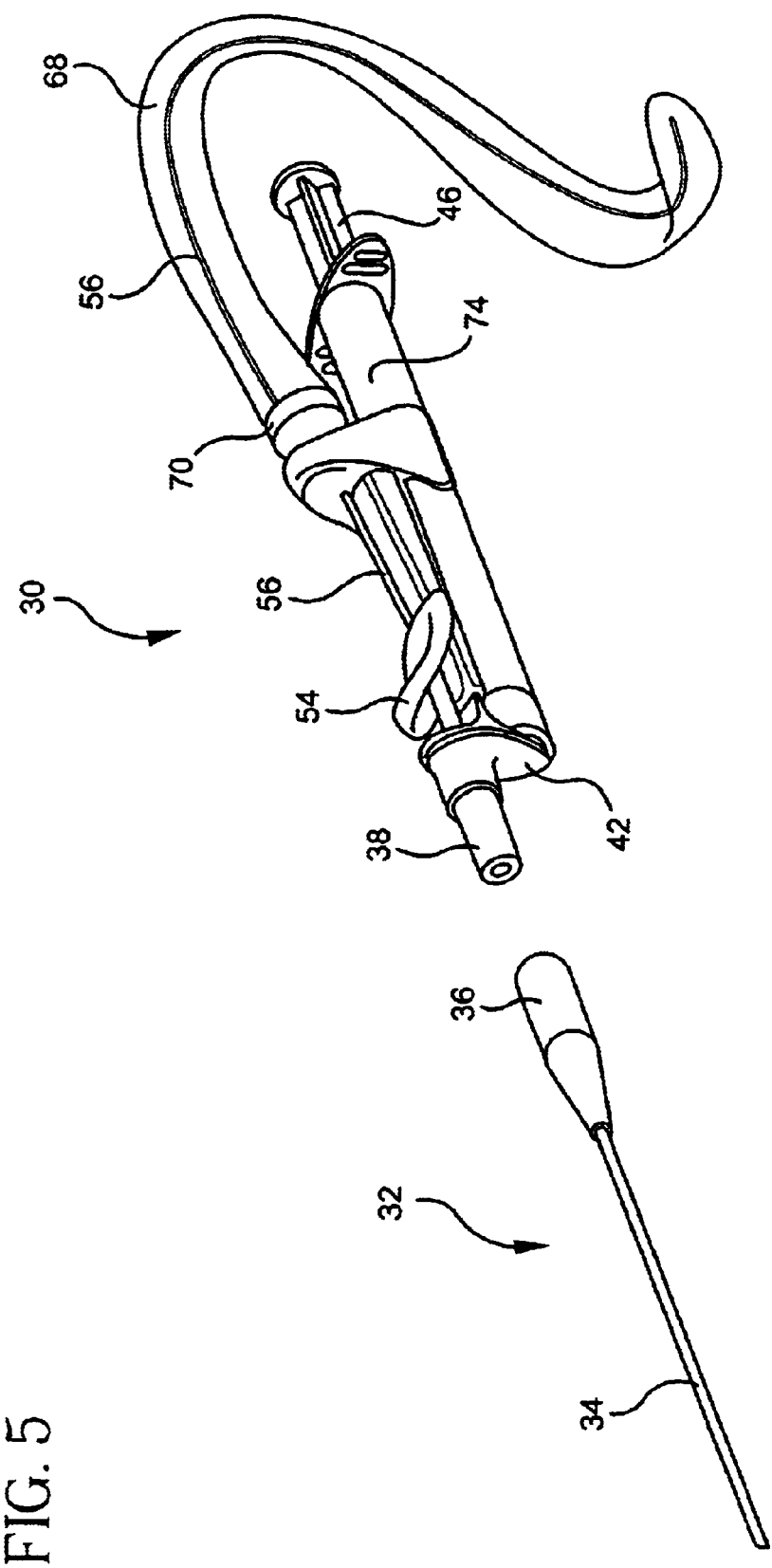
FIG. 5 is a perspective sketch of the embodiment of FIG. 4.
Figure 6:
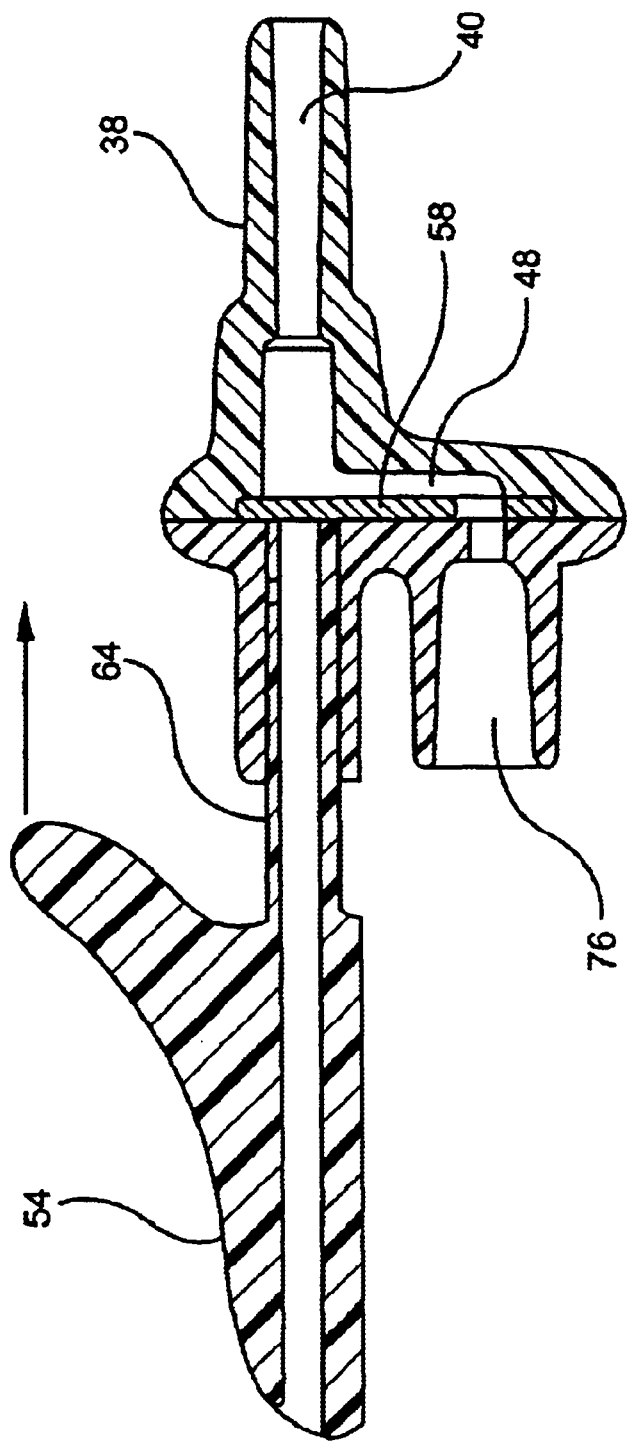
FIG. 6 is an enlarged, side cross sectional view of a portion of the embodiment of FIGS. 4 an 5.

Turning now to FIGS. 4–6, there is shown a further embodiment of the present invention and wherein like numerals have been applied to the same feature, wherever possible, for convenience. In this embodiment, many of the components are similar to the prior embodiment and include a hollow needle 34 and a needle hub 36 that extend outwardly for introduction into the blood vessel of the patient. The needle assembly 32 is affixed to the end of a needle hub support 38 where the blood aspiration canal 40 receives the blood from the patient and channels it into a passageway 48. In this embodiment, however, a commercially available syringe 74 is used and which connects to the guide wire introducer housing 42 by means of a standard female Luer fitting 76. Accordingly, the syringe 74 can be purchased by the user and adapted to be used with the guide wire introducer 30 by interfitting the distal end of the syringe 74 into the female Luer fining 76 and also by a specially constructed lug 50 that fits over the standard body of the syringe 74 and can be snapped into place holding the body of the syringe 74 in position during use.

In use, therefore, the same procedure applies to this embodiment as in the prior embodiment once the syringe 74 has been properly positioned and affixed to the guide wire introducer 30. Again, once the hollow needle 34 has been inserted into the desired blood vessel of the patient, the syringe plunger 46 is withdrawn and which causes the blood from that blood vessel to enter through the blood aspiration canal 40, the passageway 48 and into the chamber of the syringe 74. Once the user verifies the presence of the blood, it is evident that the hollow needle 34 is properly positioned and the thumb switch 54 advanced so as to pierce the seal 58 by means of the piercing cannula 64. Thus, the guide wire 56 can be manually advanced by the users thumb moving across, and frictionally engaging the guide wire 56, at the upper surface of the syringe 74. As also can be noted, the piercing cannula 64 closes off the passageway 48 at the point it communicates with the blood aspiration canal 40 and thus, again, the syringe 74 and its internal chambers are isolated and sealed off from the blood aspiration canal 40.

Figure 7:
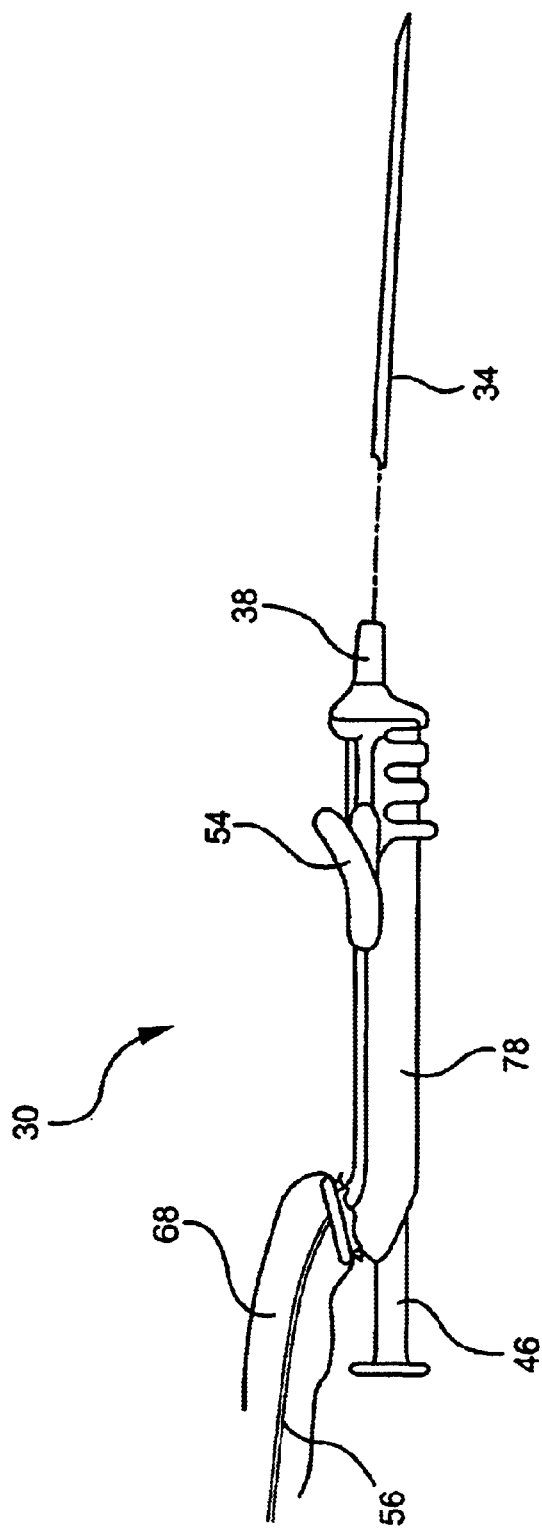
FIG. 7 is a side view of a further embodiment of the present invention.
Figure 8:
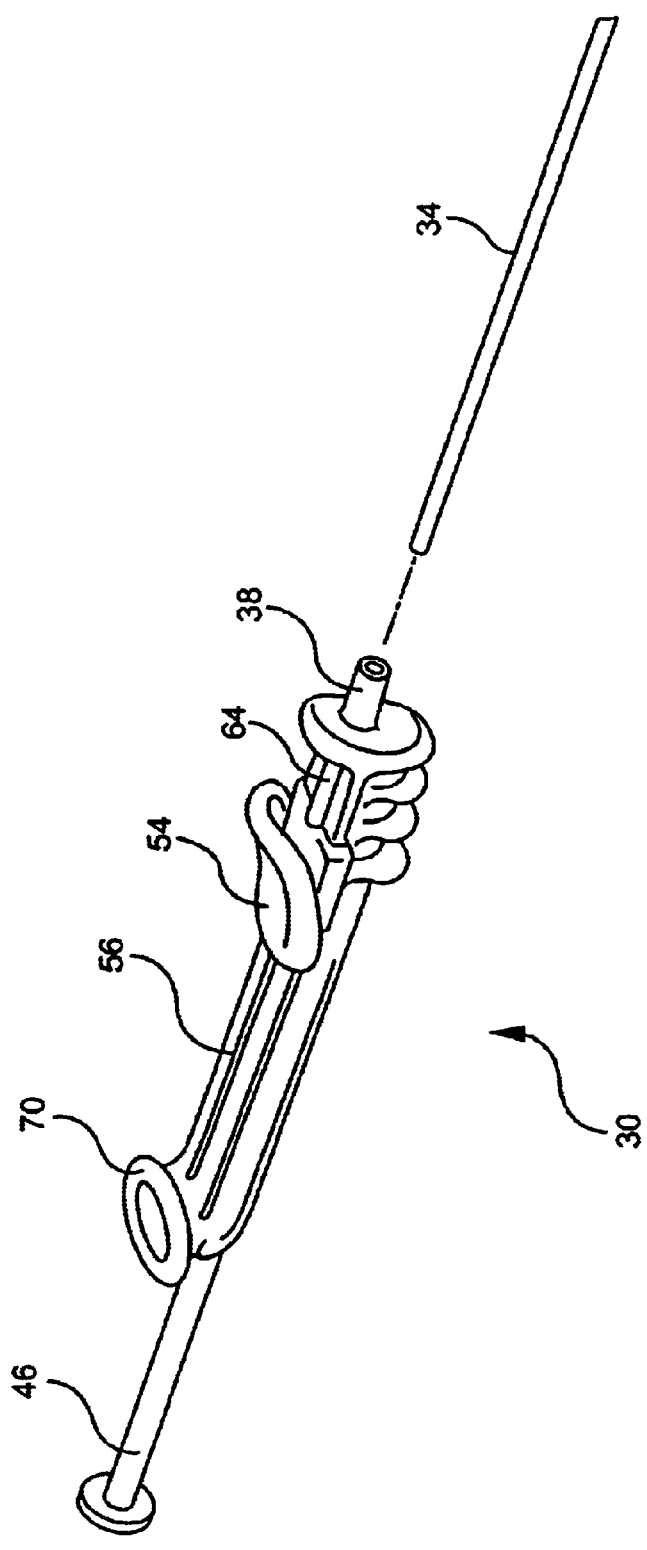
FIG. 8 is a perspective sketch of the embodiment of FIG. 7.
Figure 9:
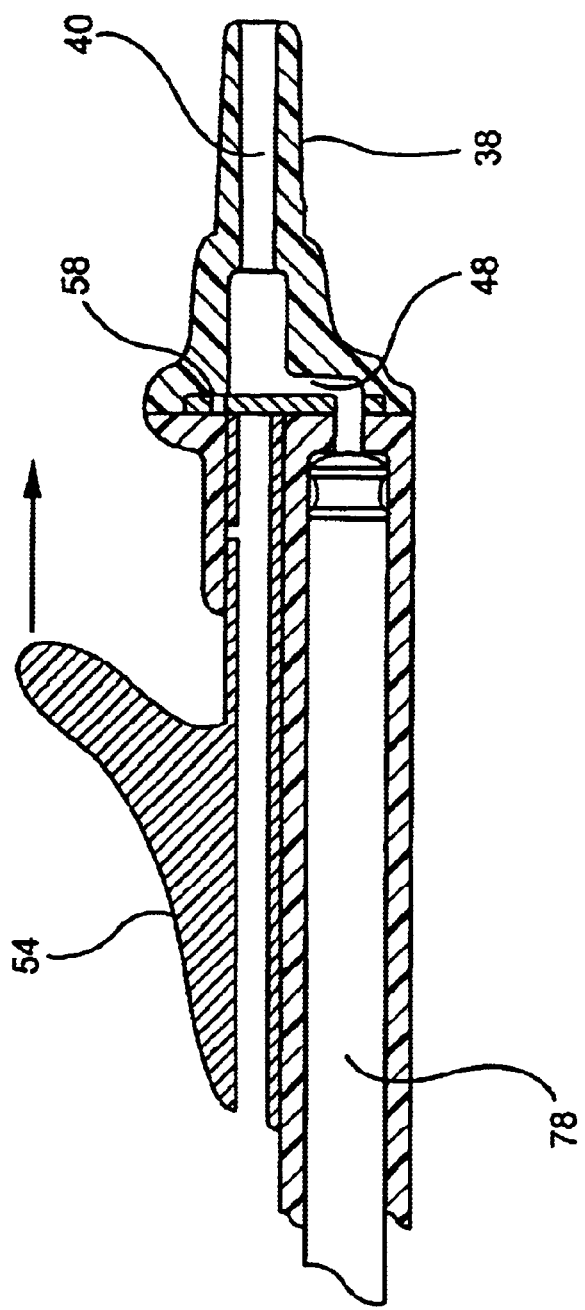
FIG. 9 is an enlarged, side cross section of a portion of the embodiment of FIGS. 7 and 8.

Turning now to FIGS. 7–9, there is shown a still further embodiment of the subject invention and wherein there is a integral syringe 78 that is molded into the guide wire introducer housing 42 as a compact integral unit. Accordingly, in this embodiment the syringe plunger 46 moves within the guide wire introducer housing 42 itself and the unit can be molded in a unitary piece. In order to accommodate the integral design, the proximal end of the guide wire introducer housing 42 is directed somewhat upwardly for attachment of the flexible envelope 68 to allow for the movement of the syringe plunger 46.

Figure 10:
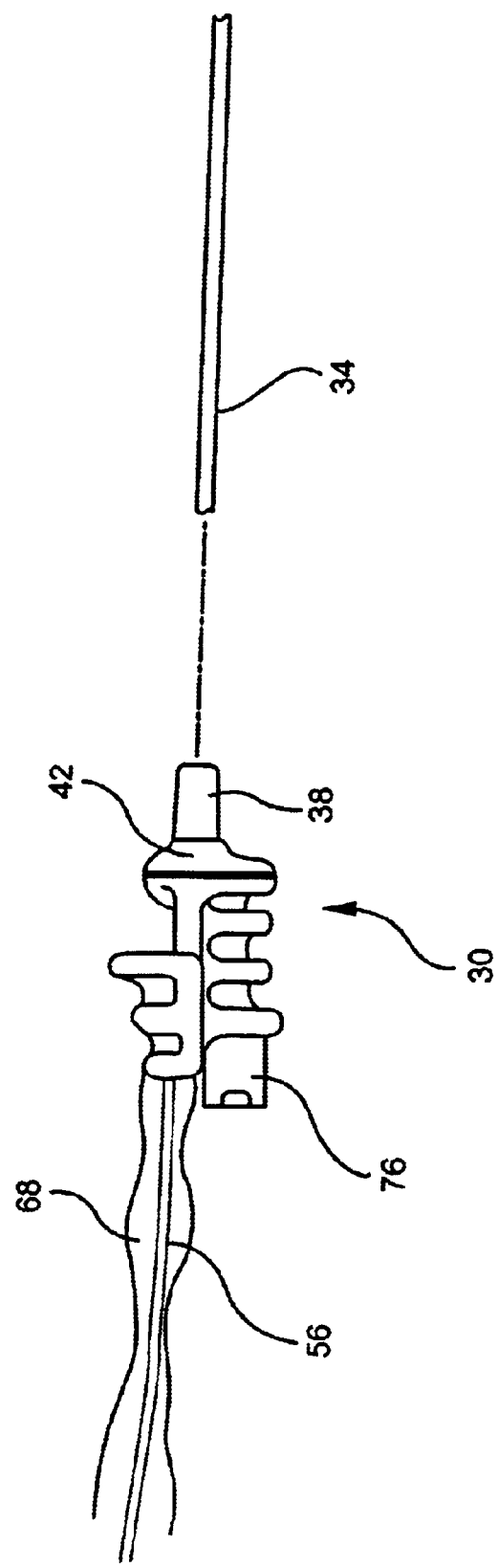
FIG. 10 is a side view of a still further embodiment of the present invention.
Figure 11:
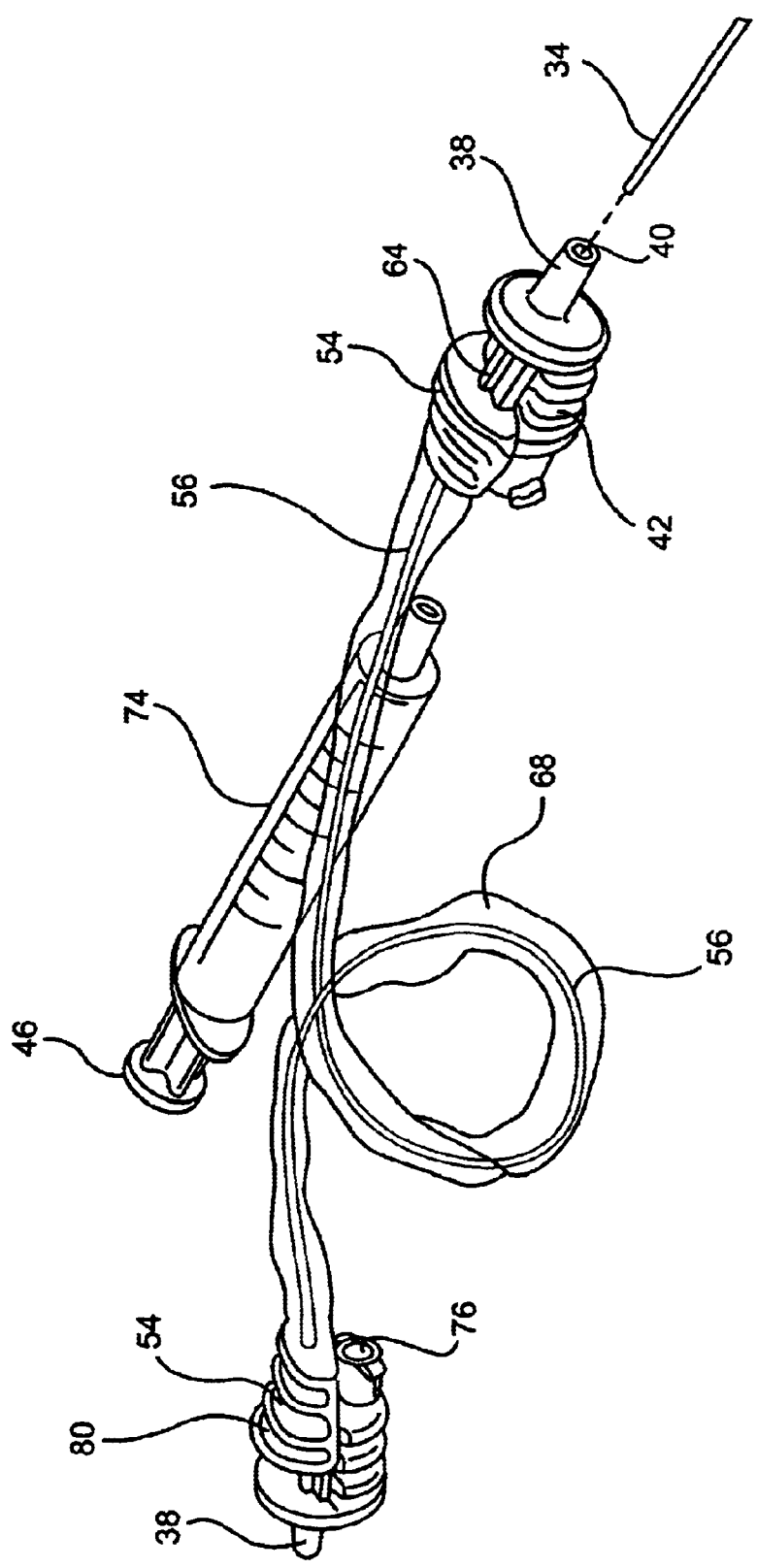
FIG. 11 is a perspective sketch of the embodiment of FIG. 10.
Figure 12:
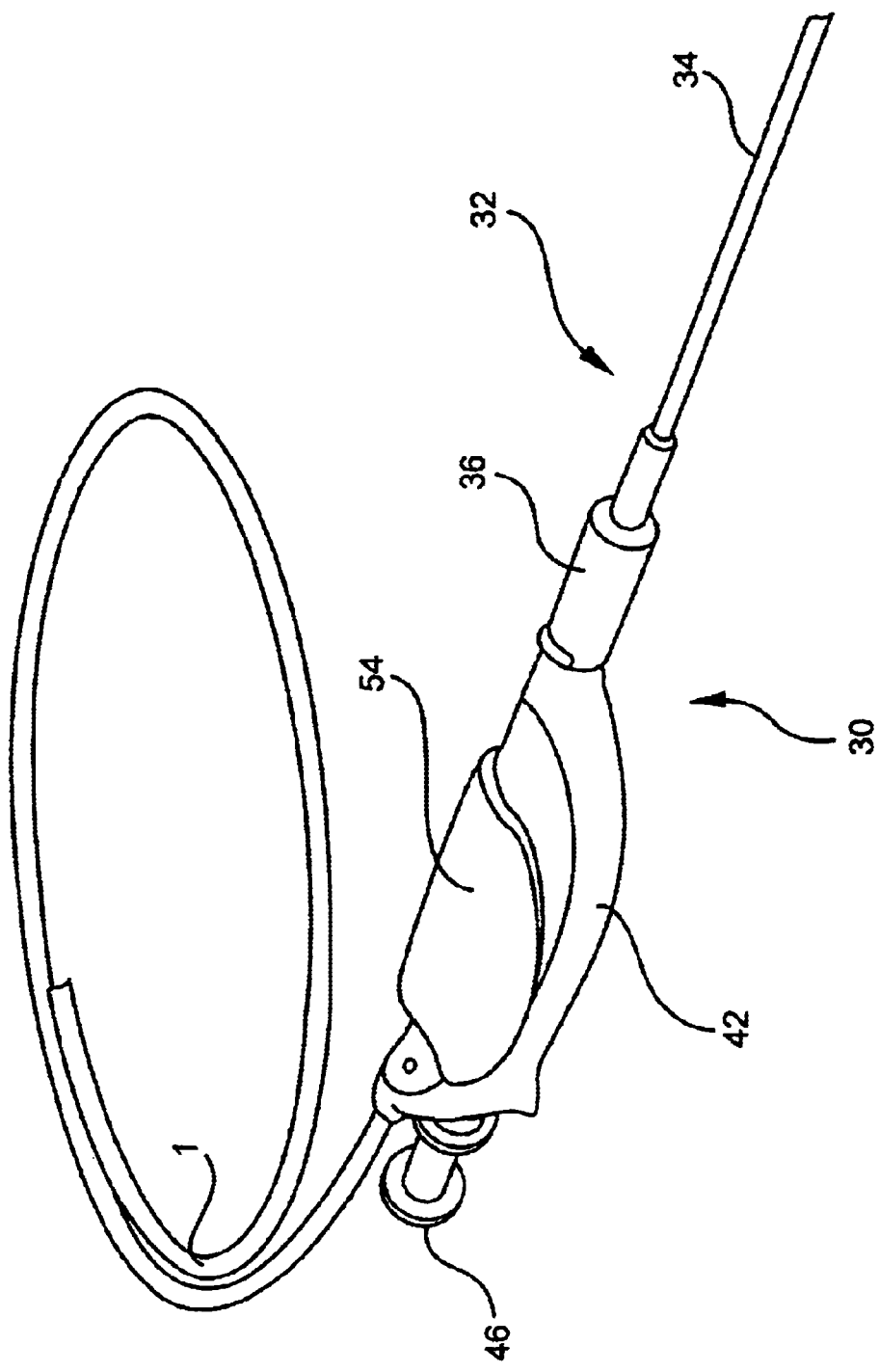
FIG. 12 is a perspective sketch of a still further embodiment of the present invention.
Figure 13:
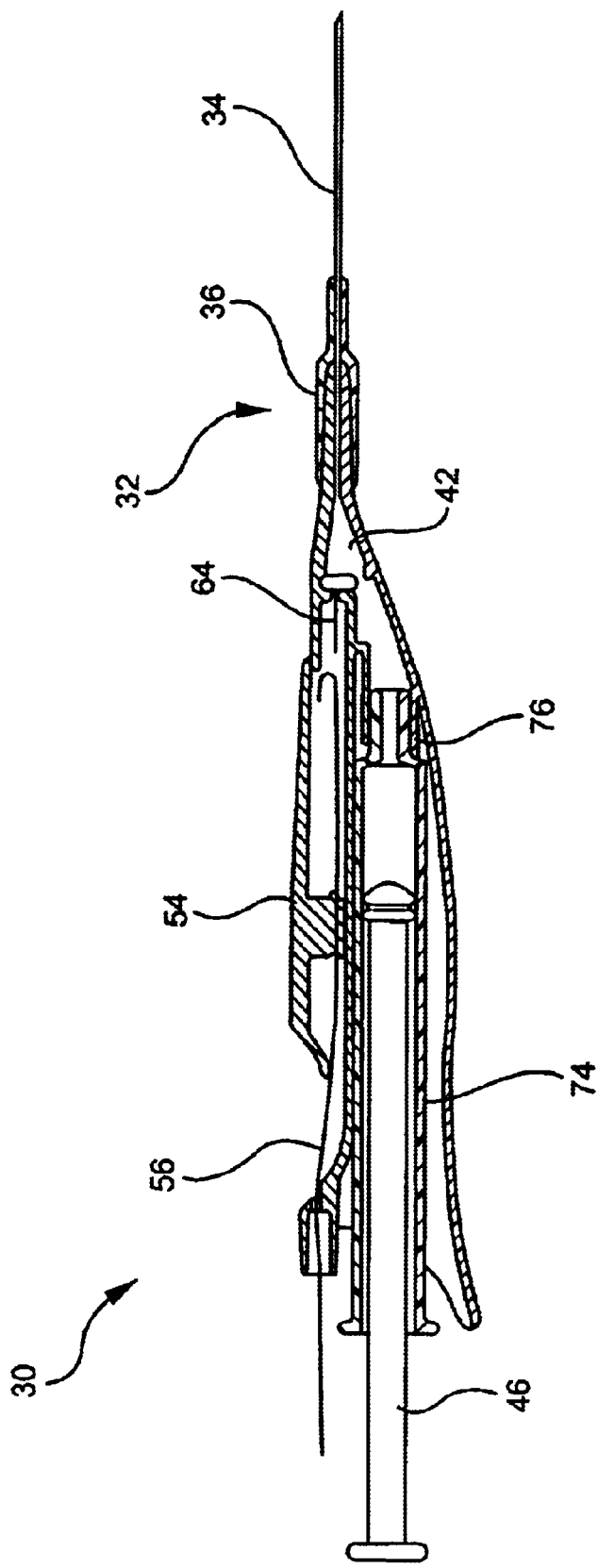
FIGS. 13–15 are enlarged, side cross sectional view of the embodiment of FIG. 12 showing various stages of use of the guide wire introducer.
Figure 14:
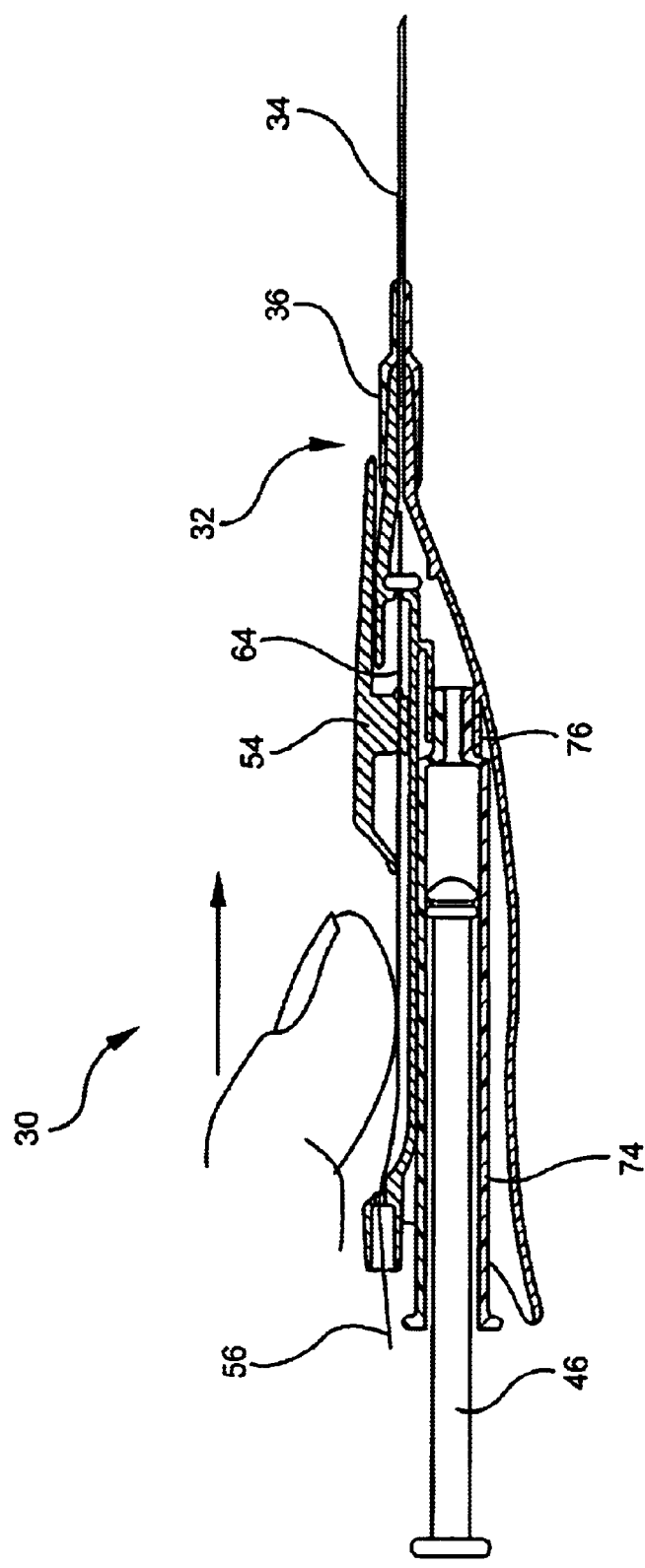
Figure 15:
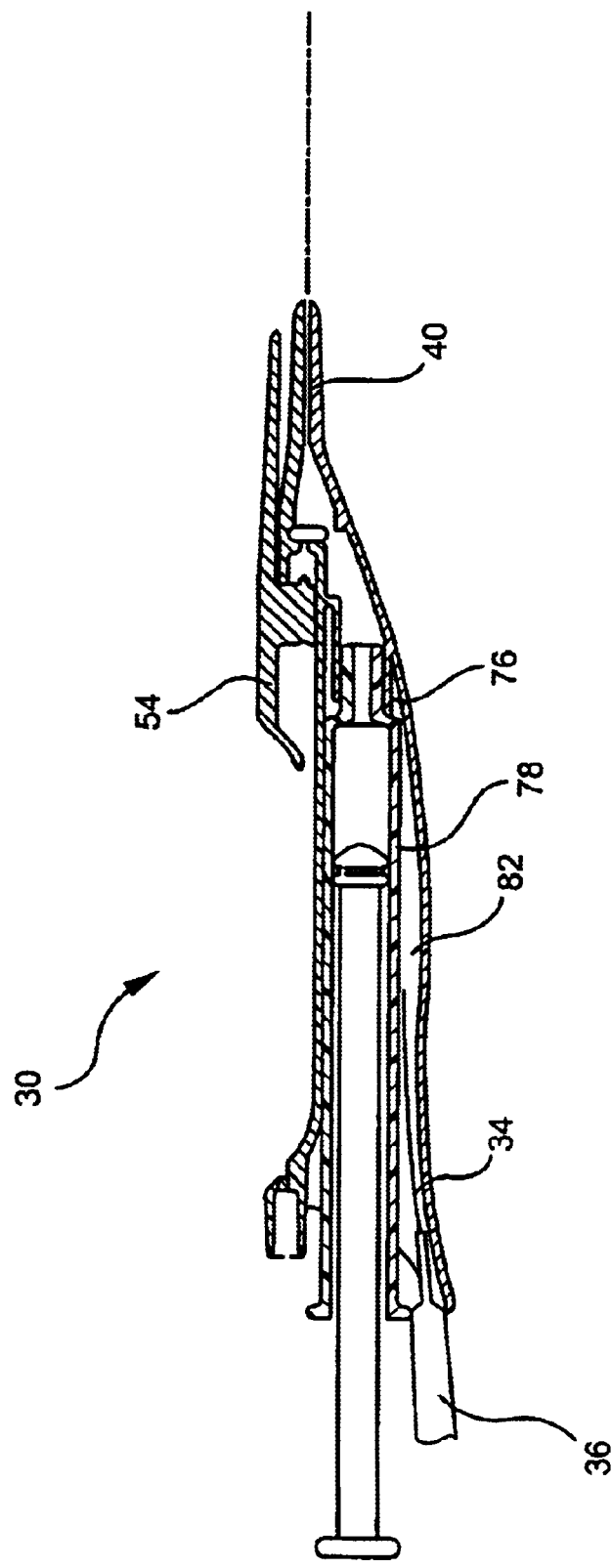

Turning now to FIGS. 10 and 11, there is shown a still further embodiment of the subject invention and where an abbreviated guide wire introducer housing 42 is used and which has a separate commercially available syringe 74 that interfits into a female Luer fitting 76 in the guide wire introducer housing 42. In this embodiment, although the various passageways are not shown in the Figures, again there is a piercing cannula that pierces a seal and which, at the same time, blocks the passageway that otherwise allows blood to pass from the needle hub support 38 to the internal chamber of the syringe 74. Those features are already shown and described with respect to the prior embodiments and are similar in the present embodiment. As a further feature, the guide wire 56 can be encased in a flexible envelope and have at its proximal end, a further guide wire introducer housing 80 that is a mirror image of the guide wire introducer housing 42 shown in the drawing as ready for use with a patient. In this manner, one end of the guide wire may be of a J end and the other can be a straight end and the user can interfit the syringe 74 to either end, thus having the option of using the straight or J end at the site without any difficult manipulation and without rising the possibility of contamination of the guide wire to select the desired end configuration of the guide wire 56.

As can be seen in this embodiment, the guide wire can be advanced by the user grasping the guide wire 56 within the flexible envelope 68 and advancing it manually since the guide wire 56 does not become exposed as in the other embodiments and the frictional engagement with the users thumb is not the method of introduction.

Turning next to FIGS. 12–15, there is shown, a further embodiment of the subject invention in which the end of the guide wire 56 can remain visible to the user prior to use so that the user can visually monitor the J tip of the guide wire 56. In this embodiment, therefore, again a standard syringe 74 can be used and which can be inserted into and intermitted with a female Luer fitting 76 in the guide wire introducer housing 42. As can be seen the thumb switch 54 is of a transparent material enabling the user to see the J end of the guide wire 56, In this embodiment, the transparent material that makes up the thumb switch 54 may be shaped so as to magnify the area of the J end of the guide wire 56 so that the visual perception of the end is enhanced. Again, in use, as the thumb switch 54 is moved toward the distal end of the guide wire introducer 30 the piercing cannula 64 straightens the J wire and, at the same time, pierces the seal 58 to seal off any passageways between the blood aspiration canal 40 within the needle hub support 38 so as to seal the blood within the syringe 74 for protection of that blood from coming in contact with the users of the device or later handlers of the device.

The magnified view created by the transparent material of the thumb switch 54 also allows the user to readily see the various markings on the guide wire 56 that allow the user can determine the length of guide wire that has been extended from the distal end of the guide wire introducer 30. Again, as can be seen, particularly in FIG. 14, once the wire has been straightened by the piercing cannula 64, it is advanced by means of the user's thumb moving the guide wire 65 as shown in the direction of the arrow A of that Figure. As a further feature of this embodiment, the guide wired introducer housing 42 may include a recess 82 so that the needle assembly 32 can be inserted into the recess 82 to prevent it from inadvertently pricking any of the users at a later time after it has been used and has been removed from the patient. In this embodiment, the guide wire 56 is encased in a standard protective tube to protect it from contamination.

Figure 16:
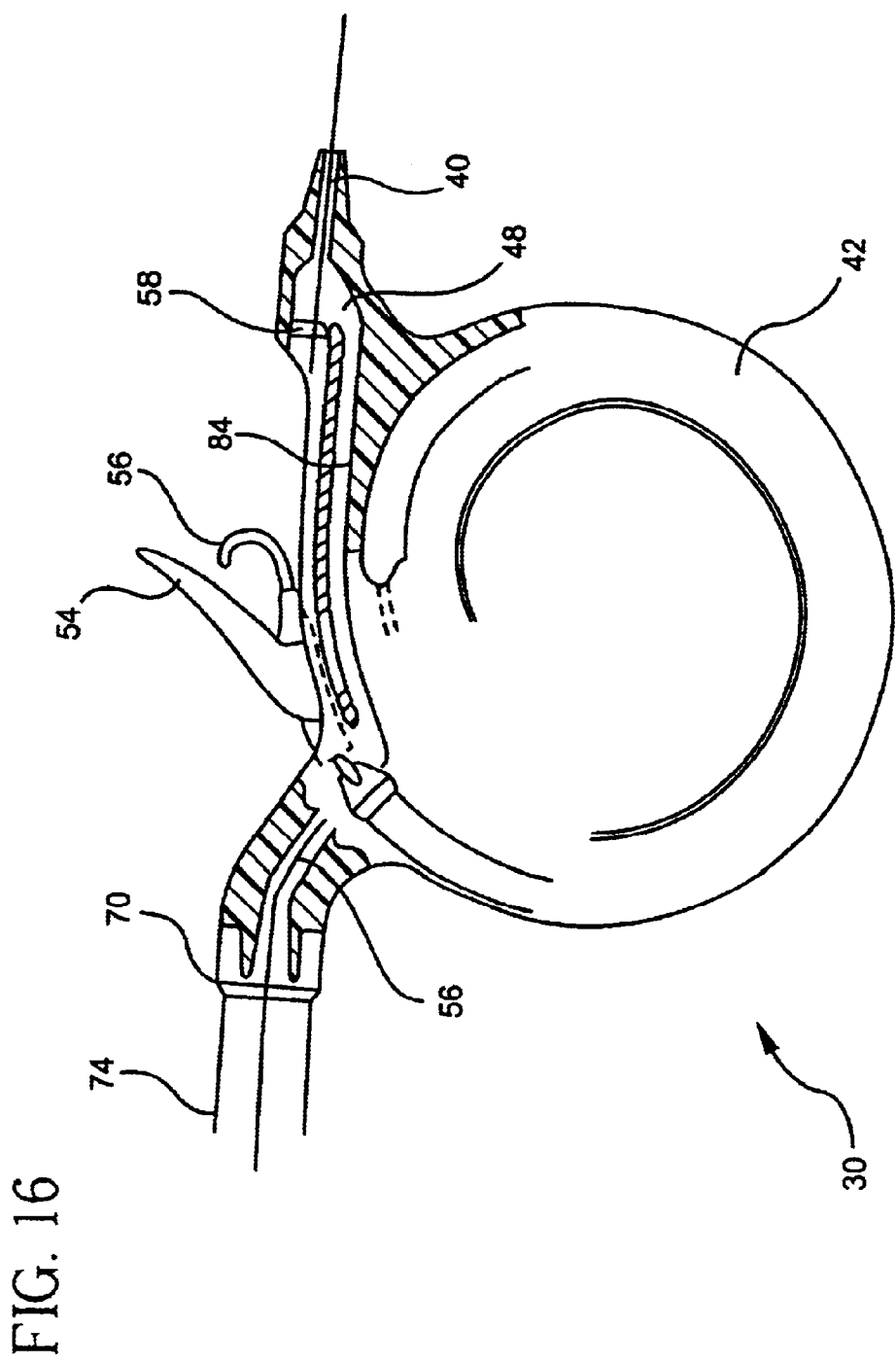
FIG. 16 is a side view of a still further embodiment of the present invention.
Figure 17:
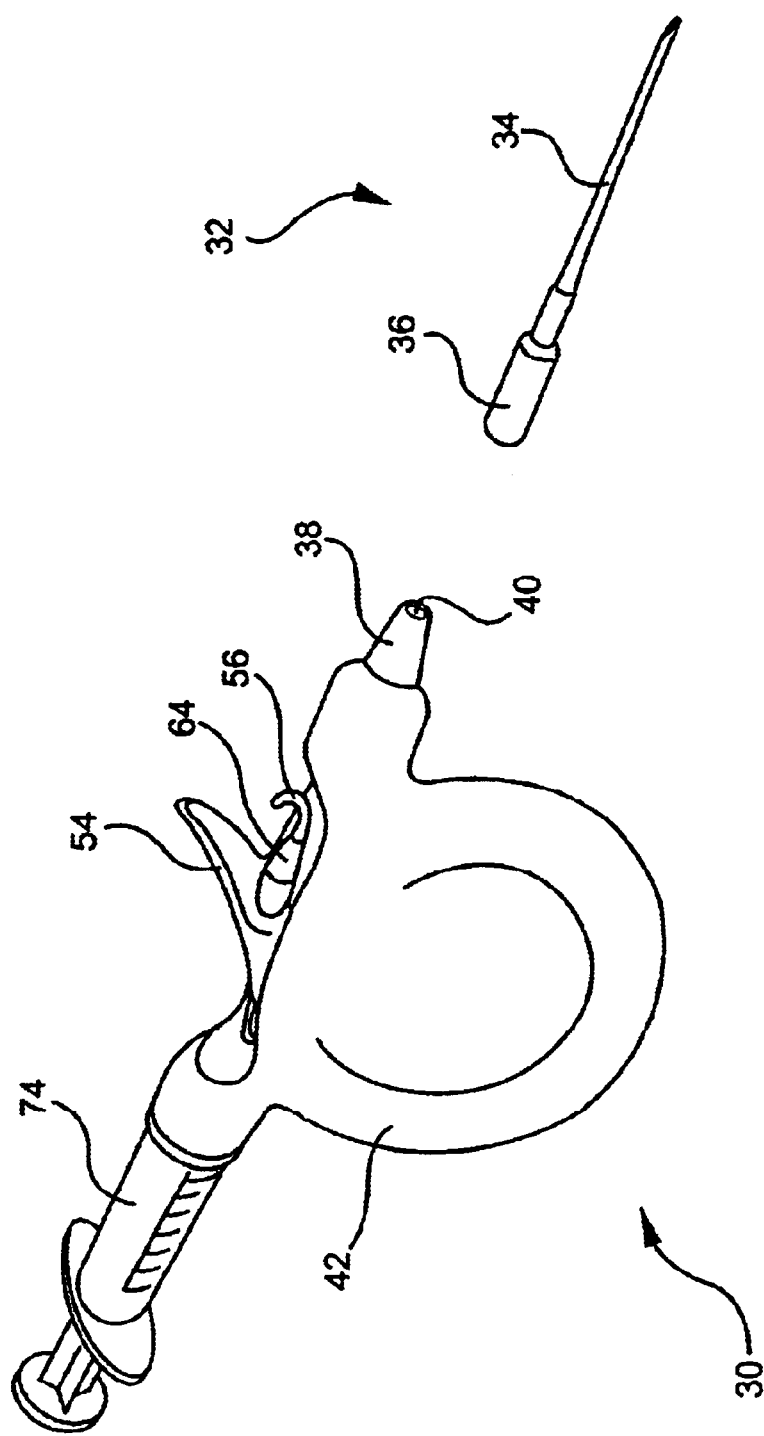
FIG. 17 is a perspective sketch of the embodiment of FIG. 16.
Figure 18:
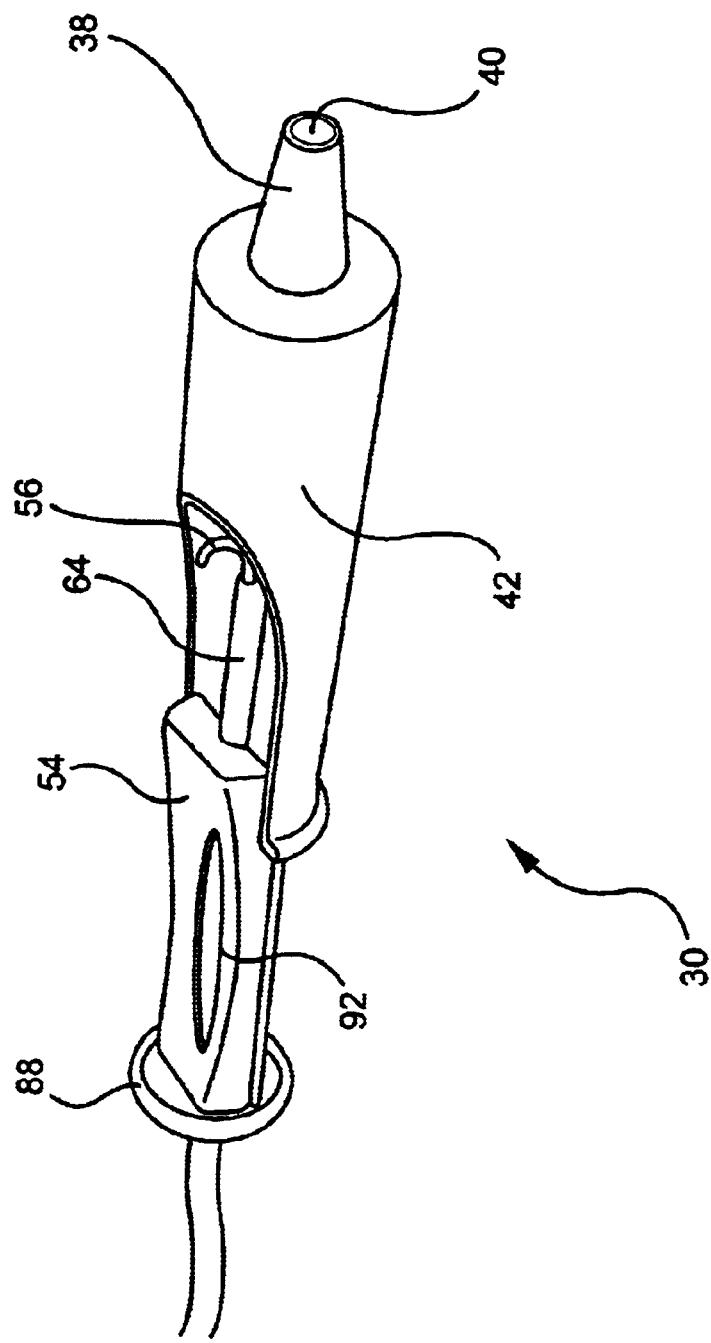
FIG. 18 is a perspective sketch of a further embodiment of the present invention.

Turning now to FIGS. 16 and 17, there is shown a still further embodiment of the present invention and wherein the guide wire introducer housing 42 has an additional appendage of a circular shape such that the guide wire 56 can be coiled and contained within the guide wire introducer housing 42 for convenience of use and to maintain it free from contamination. As is consistent with all of the embodiments, however, the thumb switch 54 is moved forwardly in the direction toward the distal end of the guide wire introducer such that the piercing cannula 64 pierces the seal 58 so that the guide wire 56 can be manually advanced by the user. In this embodiment, the syringe 74 is affixed to the proximal end of the guide wire introducer and an extended passage 84 allows the blood to flow from the needle hub support 38 to the internal chambers of the syringe. Again, as can be seen the guide wire 56 has a J end and which is straightened out as the thumb switch 54 is progressed toward the distal end of the guide wire introducer 30. Accordingly the guide wire 56 of this embodiment is contained within the molded guide wire introducer housing 42 and the device does not have the flexible envelope as in the prior embodiments. As the common feature, however the passage 84 is sealed by the piercing cannula 64 as it progresses forwardly through the seal 58 to close off any communication of blood to pass from the syringe 74 to the needle hub support 38.

Finally, turning to FIGS. 18–21C, there is shown a still further embodiment of the present invention and wherein guide wire 56 passes through an opening 86 in the syringe plunger 88. In this embodiment, the syringe again is built integral with the guide wire introducer and the thumb switch 54 moves along the upper surface of the syringe plunger 88.

Figure 21A:
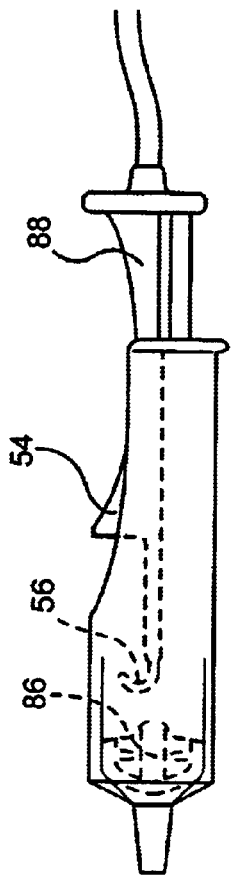
FIG. 21A–21C are schematic views of the embodiment of FIGS. 18–20 and showing the various stages of use of that embodiment.
Figure 21B:
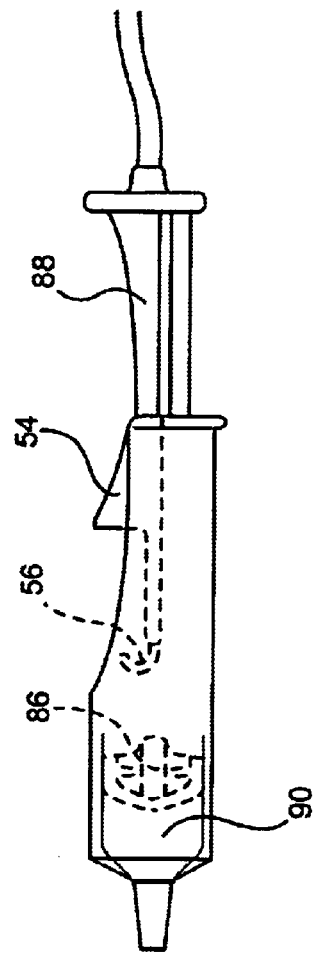
Figure 21C:
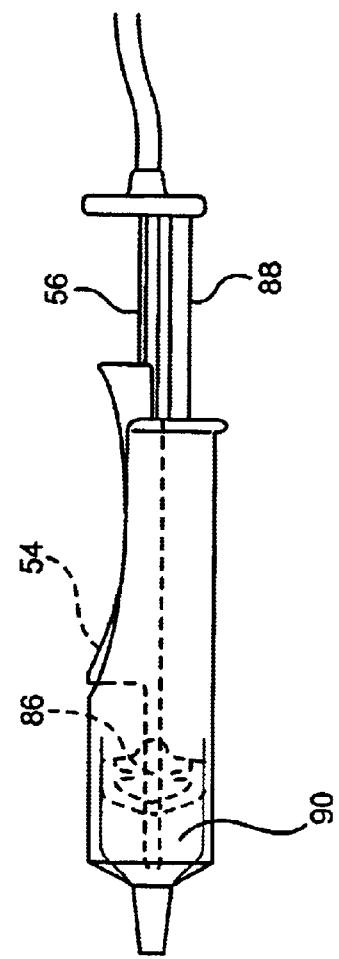

Turning specifically to FIGS. 21A, 21B and 21C, there is shown the stages of use of the guide wire introducer 30. For example, FIG. 21A shows the guide wire introducer 30 in its ready to use position, FIG. 21B shows the guide wire introducer 30 where the syringe plunger 88 been withdrawn to allow blood to enter the syringe chamber 90 and in FIG. 21C the syringe plunger 88 is still withdrawn but the thumb switch 54 has been moved by the user to its distal position where the guide wire 54 extends out through the end of the syringe plunger 88 and through the needle hub support 38 to extend the guide wire into the patient while blocking the flow of blood into or from the syringe chamber 90.

As a further feature of this embodiment, an opening 92 is formed the upper surface of the thumb switch 54 so that the user can use the thumb to frictionally engage and advance the guide wire 56 to the desired location within the patient.

While the present invention has been set forth in terms of a specific embodiment, it will be understood that the guide wire introducer herein disclosed may be modified or altered by those skilled in the art to other configurations. Accordingly, the invention is to be broadly construed and limited only by the scope and the spirit of the claims appended hereto.

What is claimed is:

1. A device for advancing a guide wire into a blood vessel of a patient comprising,
    a) a housing (42) having a proximal end and a distal end from which distal end extends a needle hub support (38) having a blood aspiration canal (40) extending along its length;
    b) a syringe chamber (44) located in the housing (42);
    c) a passageway (48) extending between the blood aspiration canal (40) and the syringe chamber (44) for the passage therethrough of aspirated blood;
    d) a switch (54) having a through hole mounted for sliding movement with respect to said housing (42) and having attached thereto a cannula (64) for movement therewith;
    e) the switch (54) being formed with the through hole aligned with the cannula (64) and the blood aspiration canal (40) for the passage therethrough of a guide wire (56); the arrangement being such that movement of the switch (54) towards the distal end of the housing (42) will cause the cannula (64) to block the passage of blood along the passageway (48) between the blood aspiration canal (40) and the syringe chamber (44).

2. A device as claimed in claim 1, in which a seal (58) is provided for preventing the flow of aspirated blood along the blood aspiration canal (40) and over the housing (42) movement of the switch (54) towards the distal end of the housing (42) causing the cannula (64) to pierce the seal (58) to allow the passage of the guide wire (56) through the blood aspiration canal (40).

3. A device as claimed in claim 1, in which lugs (50,52) are provided on the surface of the housing (42), at least one at the distal end and at least one at the proximal end of the housing (42), each lug (50, 52) being formed with a through hole in alignment with the though hole in the switch (54) for guiding the guide wire (56), and wherein the switch (54) is slidably mounted on rails (62) formed on the housing (47) between the lugs (50, 52) and over the surface of (60) of the housing, said surface being substantially flat.

4. A device as claimed in claim 1 in which an envelope (68) is attached to the proximal end of the housing (42) and surrounds that portion of the guide wire (56) extending outwardly from the proximal end of the housing.

5. A device as claimed in claim 1 wherein said syringe chamber (44) comprises a removable syringe (74) having a plunger (46) movable contained within the syringe chamber (44).

6. A device as claimed in claim 1 wherein said syringe chamber (44) is molded with the housing (42) as a unitary structure and has a syringe plunger (46) movably retained in the syringe chamber (44).

7. A device as claimed in claim 1, wherein the guide wire (56) has a J end and a straight end and wherein said housing (42) comprises two guide wire introducer housings (42), (80), each affixed to one of the ends of the guide wire (56).

8. A device as claimed in claim 1 wherein the switch (54) is transparent.

9. A device as claimed in claim 1 wherein the housing has a generally circular chamber and wherein said guide wire (56) is retained in coiled form prior to use of the device.

10. A device as claimed in claim 1 wherein the syringe chamber (90) and a plunger (88) are positioned within the housing (42) and the guide wire (56) passes through the switch (54).

11. A device as claimed in claim 10 wherein the switch (54) is mounted for sliding movement along the surface of the plunger (88).

12. A device as claimed in claim 11 wherein the switch has an opening (86) to enable manipulation of the guide wire (56) as it passes through the switch.

13. A device as claimed in claim 1 in which a needle assembly (32) is releasable supported on the needle hub support (38).

14. A device as claimed in claim 1 molded from transparent of translucent material.

15. A device for advancing a guide wire into a blood vessel of a patient comprising,
    a) a housing having a surface, a proximal end, a distal end from which extends a needle hub support having a blood aspiration canal extending along its length, and lugs on the housing surface at the housing proximal end and distal end each having a through hole in alignment with the through hole in the switch;
    b) a syringe chamber located in the housing;
    c) a passageway extending between the blood aspiration canal and the syringe chamber for the passage therethrough of aspirated blood;
    d) a switch having a through hole mounted for sliding movement with respect to said housing and having attached thereto a cannula for movement therewith;
    e) the switch being formed with a through hole aligned with the cannula and the blood aspiration canal for the passage therethrough of a guide wire; the arrangement being such that movement of the switch towards the distal end of the housing will cause the cannula to block the passage of blood along the passageway between the blood aspiration canal and the syringe chamber, and
    f) lugs on the housing surface at the housing proximal end and distal end each having a though hole in alignment with the through hole in the switch.

16. A device for advancing, a guide wire into a blood vessel of a patient comprising:

a housing having a surface, a proximal end, a distal end from which extends a needle hub support having a blood aspiration canal extending along its length;

a syringe chamber located, at least in part, within the housing;

a passageway extending between the blood aspiration canal and the syringe chamber for passage of aspirated blood;

a switch having a through hole mounted to the housing and movable with respect to the housing;

a cannula attached to the switch for movement with the switch, wherein the through hole of the switch is aligned with the cannula and the blood aspiration canal;

a guide wire passing freely through the cannula, the through hole and the blood aspiration canal without interference when the switch is positioned toward the proximal end of the housing;

wherein movement of the switch towards the distal end of the housing causes the cannula to block the passage of blood along the passageway between the blood aspiration canal and the syringe chamber while maintaining free movement of the cannula through the through hole.

* * * * *